(12) United States Patent
Kandori et al.

(10) Patent No.: US 9,101,958 B2
(45) Date of Patent: Aug. 11, 2015

(54) ELECTROMECHANICAL TRANSDUCER

(75) Inventors: Atsushi Kandori, Ebina (JP); Masao Majima, Isehara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 576 days.

(21) Appl. No.: 13/508,344

(22) PCT Filed: Dec. 3, 2010

(86) PCT No.: PCT/JP2010/007059
§ 371 (c)(1),
(2), (4) Date: May 4, 2012

(87) PCT Pub. No.: WO2011/070756
PCT Pub. Date: Jun. 16, 2011

(65) Prior Publication Data
US 2012/0218867 A1      Aug. 30, 2012

(30) Foreign Application Priority Data

Dec. 11, 2009   (JP) ................................. 2009-282279

(51) Int. Cl.
| | | |
|---|---|---|
| *G01S 15/00* | (2006.01) | |
| *B06B 1/02* | (2006.01) | |
| *G01S 15/02* | (2006.01) | |
| *G01N 29/24* | (2006.01) | |

(52) U.S. Cl.
CPC .......... *B06B 1/0269* (2013.01); *G01N 29/2412* (2013.01); *G01S 15/02* (2013.01)

(58) Field of Classification Search
USPC ....................................................... 367/157
See application file for complete search history.

(56) References Cited

U.S. PATENT DOCUMENTS 4,550,611 A   11/1985  Czarnocki ....................... 73/708
5,144,466 A   9/1992   Nakamura et al.
(Continued)

FOREIGN PATENT DOCUMENTS

| EP | 1949856 | 7/2008 |
|---|---|---|
| WO | 2004/058054 | 7/2004 |
| WO | 2008/075740 | 6/2008 |

OTHER PUBLICATIONS

International Preliminary Report on Patentability dated Jun. 21, 2012 in International Application No. PCT/JP2010/007059.
(Continued)

*Primary Examiner* — James Hulka
(74) *Attorney, Agent, or Firm* — Fitzpatrick, Cella, Harper & Scinto

(57) ABSTRACT

Provided is an electromechanical transducer which is capable of correcting or compensating a fluctuation in the transmission/reception characteristics of an elastic wave transmitting/receiving unit due to applied pressure. The electromechanical transducer (102) which transmits/receives elastic waves such as ultrasound includes the elastic wave transmitting/receiving unit (201) for transmitting/receiving elastic waves, a pressure detecting unit (203) for detecting pressure that is applied to the elastic wave transmitting/receiving unit, and a correcting unit (204). Based on pressure information which is detected by the pressure detecting unit, the correcting unit performs at least one of a correction of elastic wave transmitted/received signals relevant to the elastic wave transmitting/receiving unit and a correction of the transmission/reception characteristics of the elastic wave transmitting/receiving unit.

18 Claims, 5 Drawing Sheets

(56) References Cited

U.S. PATENT DOCUMENTS

| | | | |
|---|---|---|---|
| 5,343,314 A | 8/1994 | Nakamura et al. | |
| 5,396,360 A | 3/1995 | Majima | |
| 5,586,131 A | 12/1996 | Ono et al. | |
| 5,659,560 A | 8/1997 | Ouchi et al. | |
| 5,801,861 A | 9/1998 | Majima | |
| 7,149,442 B2 | 12/2006 | Ushijima et al. | |
| 7,382,137 B2 | 6/2008 | Ushijima et al. | |
| 7,741,851 B2 | 6/2010 | Ushijima et al. | |
| 7,872,399 B2* | 1/2011 | Kondou et al. | 310/334 |
| 8,176,780 B2 | 5/2012 | Takagi et al. | |
| 2003/0128847 A1* | 7/2003 | Smith | 381/67 |
| 2004/0228494 A1* | 11/2004 | Smith | 381/67 |
| 2006/0004290 A1 | 1/2006 | Smith et al. | 600/459 |
| 2008/0264167 A1 | 10/2008 | Kandori et al. | |
| 2009/0193893 A1 | 8/2009 | Kandori et al. | |
| 2009/0251025 A1* | 10/2009 | Kondou et al. | 310/316.01 |
| 2010/0016724 A1 | 1/2010 | Arai et al. | 600/443 |
| 2010/0213791 A1 | 8/2010 | Kandori et al. | |
| 2011/0031568 A1 | 2/2011 | Kandori et al. | |
| 2011/0169510 A1 | 7/2011 | Kandori et al. | |
| 2012/0103096 A1 | 5/2012 | Kandori | |
| 2012/0194107 A1 | 8/2012 | Kandori et al. | |

OTHER PUBLICATIONS

U.S. Appl. No. 13/566,308, filed Aug. 3, 2012 by Atsushi Kandori.

* cited by examiner

ELECTROMECHANICAL TRANSDUCER

TECHNICAL FIELD

The present invention relates to an electromechanical transducer such as an ultrasound probe for transmitting/receiving ("transmission/reception" herein means at least one of transmission and reception) ultrasound or other elastic waves, and to a measuring device that uses the electromechanical transducer.

BACKGROUND ART

There has been employed a measuring method in which an ultrasound probe is used to transmit ultrasound to an object and receive ultrasound reflected by the object, thereby obtaining information of the object (see US 2006/0004290 A1). In ultrasound diagnosis according to this measuring method, an ultrasound probe is used under a state of being pressed against a living body, which is an object to be measured, through gel or the like. Probes of this type include transmission/reception transducers for generating/detecting ultrasound, such as piezoelectric transducers (PZTs) and polymer membrane (polyvinylidene fluoride: PVDF) transducers. Other transducers for this type of ultrasound probe include capacitive micromachined ultrasonic transducers (CMUTs). CMUTs can be manufactured by a micro-electro mechanical systems (MEMS) process, which is an application of a semiconductor process, and have a wide band. A measurement with an ultrasound probe that uses a CMUT therefore yields detailed information of an object, compared to a measurement with a probe that has a narrow band.

SUMMARY OF INVENTION

Technical Problem

In a measurement with an ultrasound probe, the transmission/reception characteristics of an ultrasound transmitting/receiving unit placed on the probe's surface (transmission/reception characteristics indicating the frequency distribution of a relation between input to and output from the transmitting/receiving unit) vary depending on external pressure applied to a face of the ultrasound probe that is in contact with an object. When pressure applied to a transducer fluctuates or deviates from an expected value as this, an unintended fluctuation in transmission/reception characteristics is caused in the transducer. If imaging, for example, of an object is performed based on ultrasound information obtained with a transducer that has undergone a fluctuation in transmission/reception characteristics, the resultant image is lowered in resolution. A device disclosed in US 2006/0004290 A1 has a pressure detecting element separate from an ultrasound detecting element. However, the pressure detecting element is an element for detecting whether the ultrasound detecting element is in contact with an object appropriately, and is not designed to solve a problem concerning the unintended fluctuation in transmission/reception characteristics.

Solution to Problem

In view of the problem described above, an electromechanical transducer according to the present invention performs at least one of transmission and reception of elastic waves such as sound waves, ultrasound, or acoustic waves, and includes an elastic wave transmitting/receiving unit, which transmits/receives elastic waves, a pressure detecting unit, which detects pressure applied to the elastic wave transmitting/receiving unit, and a correcting unit. Based on pressure information which is detected by the pressure detecting unit, the correcting unit performs at least one of a correction of elastic wave transmitted/received signals relevant to the elastic wave transmitting/receiving unit and a correction of the transmission/reception characteristics of the elastic wave transmitting/receiving unit. In view of the problem described above, a measuring device according to the present invention includes the electromechanical transducer. The measuring device also includes an imaging unit for imaging an object by correcting an imaging information signal, which is created based on an elastic wave received signal from the electromechanical transducer, with an image correcting signal, which is created based on the pressure information from the electromechanical transducer.

Advantageous Effects of Invention

According to the present invention, a fluctuation in transmission/reception characteristics due to pressure externally applied to the elastic wave transmitting/receiving unit of the electromechanical transducer can be corrected or compensated based on the pressure information detected by the pressure detecting unit. Accurate elastic wave information is consequently obtained despite external pressure working on the electromechanical transducer. Therefore, in the case where imaging, for example, of an object is performed based on elastic wave information obtained by the electromechanical transducer, the resultant image is less lowered in resolution and more accurate information on the object is obtained.

Further features of the present invention will become apparent from the following description of exemplary embodiments with reference to the attached drawings.

DESCRIPTION OF EMBODIMENTS

Figure 1A:
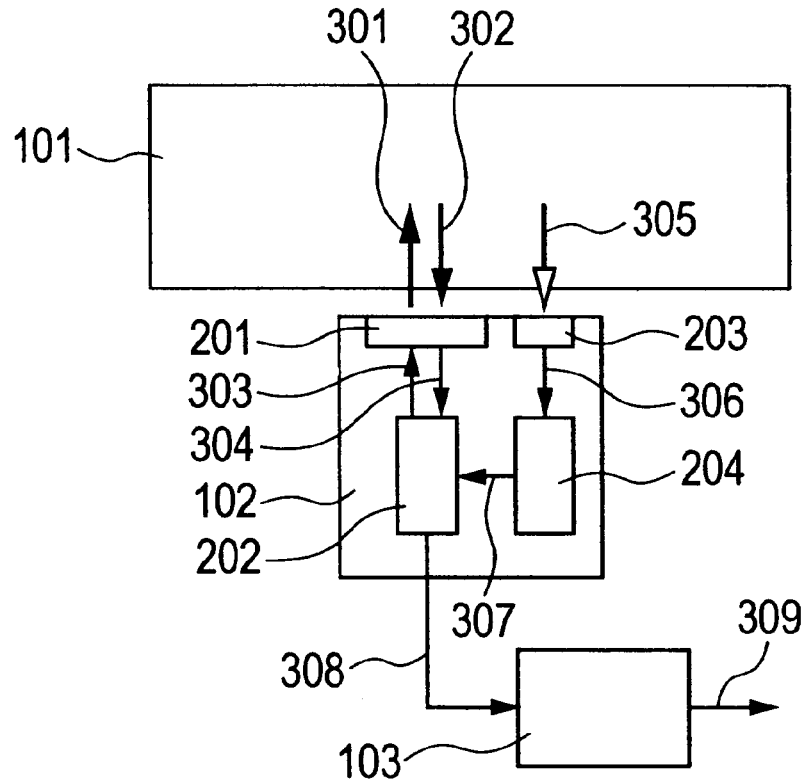
FIG. 1A is a diagram illustrating an electromechanical transducer according to a first embodiment and a modification example thereof.

Embodiments of the present invention are described below. An important point of the present invention is that at least one of a correction of elastic wave transmitted/received signals relevant to a transmitting/receiving unit (i.e., at least one of a transmitted signal which is input to the transmitting/receiving unit and a received signal which is output from the transmitting/receiving unit) and a correction of the transmission/reception characteristics of the transmitting/receiving unit is made based on detected pressure information. In other words, in an electromechanical transducer according to the present invention, a pressure detecting unit for detecting pressure is provided separately from a transmitting/receiving unit that detects/transmits elastic waves, and pressure information obtained by the pressure detecting unit is fed back for a correction or compensation of the transmission/reception characteristics of the transmitting/receiving unit. A correction of the transmission/reception characteristics of the elastic wave transmitting/receiving unit here refers to correcting a fluctuation in transmission/reception characteristics by controlling the transmitting/receiving unit. On the other hand, compensation of the transmission/reception characteristics of the elastic wave transmitting/receiving unit refers to indirectly correcting a fluctuation in transmission/reception characteristics by correcting a transmitted signal which is transmitted to the transmitting/receiving unit, or correcting a received signal which is to be received by the transmitting/receiving unit, while leaving the fluctuation in the transmission/reception characteristics of the transmitting/receiving unit as it is. Usually, only one of the correction and the compensation is executed. In the case where the correction or the compensation alone is not enough for satisfactory correction, or when otherwise required by the circumstances, both of the correction and the compensation may be executed.

Based on the concept described above, a basic mode of an electromechanical transducer according to the present invention includes an elastic wave transmitting/receiving unit which transmits/receives ultrasound, a pressure detecting unit which detects pressure applied to the elastic wave transmitting/receiving unit, and a correcting unit. Based on pressure information which is detected by the pressure detecting unit, the correcting unit performs at least one of a correction of elastic wave transmitted/received signals relevant to the elastic wave transmitting/receiving unit and a correction of the transmission/reception characteristics of the elastic wave transmitting/receiving unit. In a basic mode, a measuring device according to the present invention includes the electromechanical transducer. The measuring device also includes an imaging unit for imaging an object by correcting an imaging information signal, which is created based on an elastic wave received signal from the electromechanical transducer, with an image correcting signal, which is created based on the pressure information from the electromechanical transducer.

The basic modes can be developed into embodiments described below. For example, the transmitting/receiving unit may be structured to include a capacitive transducer that has multiple electrodes facing each other with a gap interposed in between, while the correcting unit is structured to correct the transmission/reception characteristics of the transmitting/receiving unit by changing a bias voltage between the electrodes or other parameters and thus changing the electrostatic attractive force (see a second embodiment described below). The correcting unit may also be structured to correct at least one of an elastic wave transmitted signal which is transmitted to the transmitting/receiving unit and an elastic wave received signal which is received by the transmitting/receiving unit (see a first embodiment and other embodiments described below).

The pressure detecting unit may have frequency characteristics that respond to pressure of a frequency lower than a frequency range usable in the frequency characteristics of the transmitting/receiving unit (namely, the frequency distribution of the transmission/reception characteristics) (see a third embodiment and other embodiments described below). The pressure detecting unit may also be structured to include a capacitive transducer that contains multiple electrodes facing each other (see the third embodiment and other embodiments described below). In this case, the pressure detecting unit may be structured to include a modulating unit, which modulates a capacitance between the electrodes with the use of a signal having a predetermined frequency, and a demodulating unit, which uses a signal having a predetermined frequency to demodulate a current signal from the transducer in which a signal having a predetermined frequency is multiplexed (see a fourth embodiment described below). The predetermined frequency is higher than a frequency range usable in the frequency characteristics of the pressure detecting unit, and is outside the frequency range usable in the frequency characteristics of the transmitting/receiving unit. A structure including multiple transmitting/receiving units and multiple pressure detecting units may be built in which the correcting unit is structured to perform the correction described above for each of the multiple transmitting/receiving units based on pieces of pressure information respectively detected by each of the multiple pressure detecting units (see a fifth embodiment described below).

A detailed description on electromechanical transducers according to embodiments of the present invention is given below with reference to the drawings.

First Embodiment

As can be seen in FIG. 1A, which illustrates an electromechanical transducer according to a first embodiment, the transmission/reception characteristics of an elastic wave transmitting/receiving unit 201 is compensated in this embodiment based on pressure information provided by a pressure detecting unit 203, which detects pressure 305 applied to the elastic wave transmitting/receiving unit 201. In FIG. 1A, denoted by 101, 102, 103, and 202 are, respectively, an object to be measured such as a living body, the electromechanical transducer, an imaging unit, and a driving and detected signal processing unit for processing a transmitted signal 303 and a received signal 304 which are relevant to the transmitting/receiving unit 201. Denoted by 204, 301, 302, and 306 are, respectively, a correcting unit for compensating the transmission/reception characteristics of the transmitting/receiving unit 201, transmitted ultrasound, received ultrasound, and a detected pressure signal which is from the pressure detecting unit 203. Denoted by 307, 308, and 309 are, respectively, a correcting signal for correcting transmitted/received signals, an imaging information signal, which is output from the driving and detected signal processing unit 202 to the imaging unit 103, and an imaging signal, which is created by the imaging unit 103 based on the imaging information signal 308.

The electromechanical transducer 102 in this embodiment includes the transmitting/receiving unit 201, the signal processing unit 202, the pressure detecting unit 203, and the correcting unit 204, and is placed in contact with the object 101. The transmitting/receiving unit 201 transmits ultrasound toward the object 101, and receives ultrasound that arrives from inside the object 101 through reflection or other actions. The transmitting/receiving unit 201 transmits ultrasound when driven by an input of the ultrasound transmitted signal 303 from the signal processing unit 202. The transmitting/receiving unit 201 receives ultrasound and outputs the ultrasound received signal 304 to the signal processing unit 202. The frequency of ultrasound transmitted/received here is usually within a range of 1 MHz to 10 MHz. The elastic wave transmitting/receiving unit 201 can be a piezoelectric transducer such as a PZT, a polymer transducer such as a PVDF transducer, or a capacitive transducer.

The pressure detecting unit 203 detects the pressure 305 applied externally to the elastic wave transmitting/receiving unit 201, and outputs the detected pressure signal 306 to the correcting unit 204. The pressure detecting unit 203 can take any form as long as the pressure detecting unit is capable of detecting the pressure 305 applied to the transmitting/receiving unit 201. The correcting unit 204 stores a relation between the varying pressure 305 and the transmission/reception characteristics of the elastic wave transmitting/receiving unit 201. The transmission/reception characteristics indicate the relation of an output signal to an input signal that is input to the elastic wave transmitting/receiving unit 201. For example, the transmission/reception characteristics indicate the relation of an output wave to an input electrical signal, or the relation of an output electrical signal to an input wave. The correcting unit 204 in this embodiment creates, based on the stored relation, from the detected pressure signal 306, the correcting signal 307 for signal correction in the signal processing unit 202, and outputs the correcting signal 307 to the signal processing unit 202.

The signal processing unit 202 adjusts the ultrasound transmitted signal 303 based on the transmission/reception correcting signal 307, and outputs the adjusted ultrasound transmitted signal 303 to the transmitting/receiving unit 201. The signal processing unit 202 adjusts the ultrasound received signal 304, which is received by the transmitting/receiving unit 201, based on the transmission/reception correcting signal 307 to create the imaging information signal 308. The imaging information signal 308 output from the signal processing unit 202 is sent from a probe of the electromechanical transducer 102 to the imaging unit 103, where imaging of the object 101 is performed and the imaging signal 309 is output. Because the relation between pressure applied to the transmitting/receiving unit 201 and the transmission/reception characteristics of the transmitting/receiving unit 201 is known in advance, the transmission/reception characteristics can be compensated by adjusting or correcting the ultrasound transmitted signal 303 and/or the ultrasound received signal 304 based on the detected pressure signal 306. For instance, in the case where the efficiency of ultrasound transmission/reception drops as the pressure 305 becomes smaller, a correction is made as follows. That is, the signal processing unit 202 adjusts transmitted ultrasound by increasing the amplitude of the transmitted signal 303, or increases the magnification in a conversion of the received signal 304 into the imaging information signal 308. In this manner, a change in the transmission/reception characteristics of the elastic wave transmitting/receiving unit 201 is compensated based on the pressure signal 306 by performing at least one of a correction of the ultrasound transmitted signal 303 and a correction of the ultrasound received signal 304 on the transmitting/receiving unit 201.

In this embodiment, instead of correcting a fluctuation in the transmission/reception characteristics of the transmitting/receiving unit 201 itself, a correction of the ultrasound transmitted signal 303 which is transmitted to the transmitting/receiving unit 201 and/or a correction of the ultrasound received signal 304 which is received by the transmitting/receiving unit 201 is performed, to thereby ultimately compensate a change in the transmission/reception characteristics of the transmitting/receiving unit 201. The time how long the pressure detecting unit 203 and the correcting unit 204 are to operate can be set in various manners in this embodiment. For example, when the pressure detecting action of the pressure detecting unit 203 and the received ultrasound 302 have little interaction to each other, the pressure detecting unit 203 can keep operating during the transmitting/receiving unit 201 is in operation, so that the correction described above can be executed in real time (see the third embodiment and other embodiments described below). When there is a fear of the interaction, on the other hand, the pressure detecting unit 203 may be put into operation at regular or irregular intervals while the transmitting/receiving unit 201 stops operating, so that the correcting unit 204 sets settings relevant to the correction described above in the signal processing unit 202 during that time. The pressure detecting unit 203 may also be put into operation at the time the transmitting/receiving unit 201 starts operating, so that the correcting unit 204 sets settings relevant to the correction described above in the signal processing unit 202 at that point.

Figure 1B:
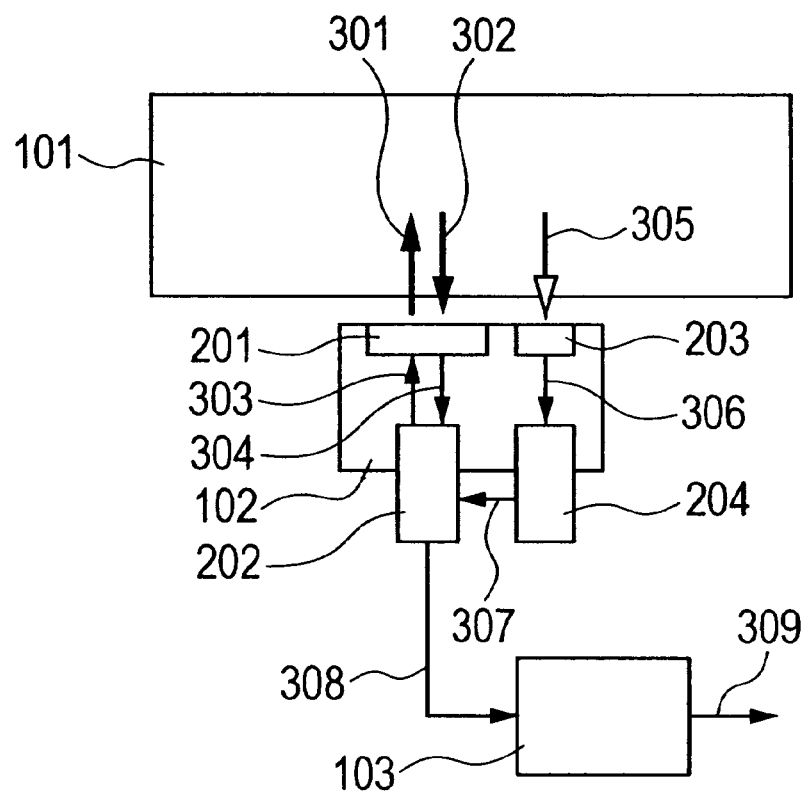
FIG. 1B is a diagram illustrating an electromechanical transducer according to a first embodiment and a modification example thereof.

While the electromechanical transducer 102 of this embodiment illustrated in FIG. 1A includes the elastic wave transmitting/receiving unit 201, the signal processing unit 202, the pressure detecting unit 203, and the correcting unit 204, a structure illustrated in FIG. 1B may also be employed. In the structure of FIG. 1B, a part of the correcting unit 204 and a part of the signal processing unit 202 are placed outside of the electromechanical transducer 102. This way, the load of signal processing in the electromechanical transducer 102 is lessened and the structure of the electromechanical transducer 102 is simplified. The electromechanical transducer 102 can thus be made further smaller in size.

According to this embodiment, a correction of a transmitted signal which is transmitted to the transmitting/receiving unit and/or a correction of a received signal which is received by the transmitting/receiving unit 201 is performed based on pressure information which is detected by the pressure detecting unit. A fluctuation in transmission/reception characteristics due to pressure applied to the transmitting/receiving unit of the electromechanical transducer is thus compensated, and accurate elastic wave information is obtained even when pressure works on the electromechanical transducer.

Second Embodiment

A second embodiment is described next with reference to FIG. 2A. The second embodiment differs from the first embodiment in terms of the structure of the elastic wave transmitting/receiving unit 201 and how a fluctuation in the transmission/reception characteristics of the transmitting/receiving unit is dealt with. The rest of the second embodiment is the same as the first embodiment. In this embodiment, a CMUT which is a type of capacitive transducer is used in the elastic wave transmitting/receiving unit 201, and the transmission/reception characteristics of the transmitting/receiving unit 201 are corrected directly by changing the electrostatic attractive force between electrodes of the CMUT.

Figure 2A:
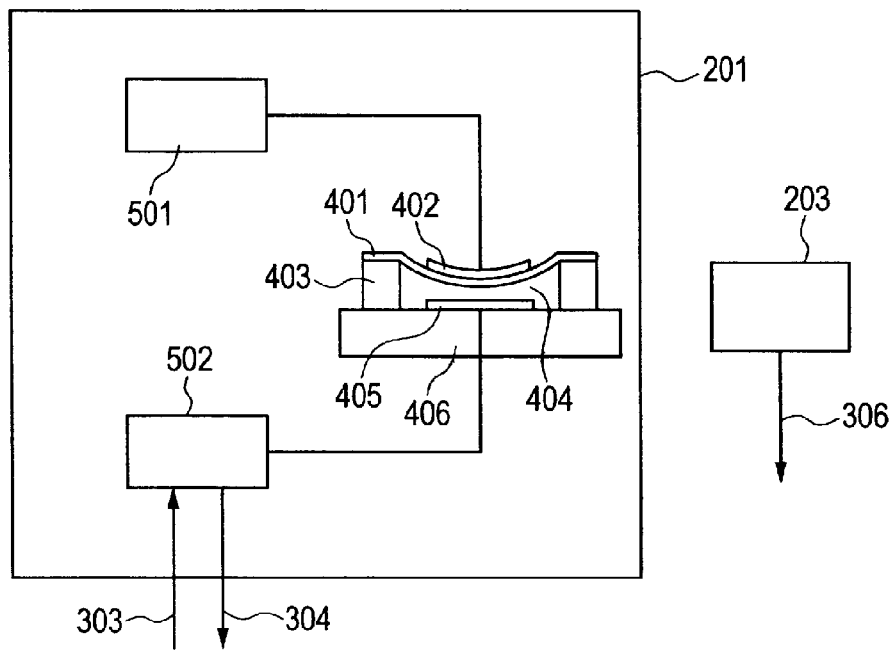
FIG. 2A is a diagram illustrating an electromechanical transducer according to a second embodiment.

In FIG. 2A which illustrates this embodiment, the transmitting/receiving unit 201 includes a diaphragm 401, an upper electrode 402, supporting portions 403, a gap 404, a lower electrode 405, and a substrate 406. Denoted by 501 and 502 are, respectively, a DC potential applying unit 501 of the transmitting/receiving unit 201 and a signal processing unit of the transmitting/receiving unit 201. In this elastic wave transmitting/receiving unit 201, the upper electrode 402 is formed on the diaphragm 401, which is supported by the supporting portions 403 formed on the substrate 406. The lower electrode 405 is placed on the substrate 406 so as to face the upper electrode 402, which is formed on the diaphragm 401, via the gap 404 (usually several tens nm to several hundreds nm). The mode of the diaphragm 401 is set to a numerical value that facilitates vibration at the frequency of ultrasound transmitted/received (usually about 1 MHz to 10 MHz). CMUTs are wider in band than PZTs and other similar transducers. Using a CMUT as the transducer accordingly means that ultrasound can be transmitted/received in a wider band and that an object can be, for example, imaged with more detailed information.

The DC potential applying unit 501 applies a predetermined DC potential to the upper electrode 402 so that a desired potential difference is created between the upper electrode 402 and the lower electrode 405. The signal processing unit 502 applies the AC driving signal 303 to the lower electrode 405, to thereby generate alternate-current electrostatic attractive force between the electrodes and cause the diaphragm 401 to vibrate at a certain frequency. The ultrasound 301 is thus transmitted. The received ultrasound 302 causes the diaphragm 401 to vibrate, thereby generating a minute current in the lower electrode 405 through electrostatic induction. The minute current is processed by the signal processing unit 502 to take out the ultrasound received signal 304 (as for the ultrasound 301 and the ultrasound 302, see FIGS. 1A and 1B).

A relation between the transmission/reception characteristics of the CMUT and applied pressure in this embodiment is described. Usually, pressure within the gap 404 of a cell is reduced compared with external pressure, and a force generated from the difference between the external pressure and the internal pressure of the gap 404 bends the diaphragm 401 toward the substrate 406. The bending amount of the diaphragm 401 is determined, when the applied pressure is the same, by mechanical characteristics brought about by such parameters as the size, shape, thickness, and film quality of the diaphragm. While the CMUT is in operation, as described above, a predetermined potential difference is applied between the upper and lower electrodes, and the electrostatic attractive force generated between the electrodes further bends the diaphragm 401, in addition to the original bend by the external pressure, toward the substrate 406. This is for enhancing the efficiency of ultrasound transmission/reception. In the transmission of the ultrasound 301, the electrostatic attractive force between the electrodes is in inverse proportion to the square of the distance between the electrodes, and therefore a high efficiency is obtained by closing the distance between the electrodes. In the reception of the ultrasound 302, the magnitude of a minute current detected is in inverse proportion to the distance between the electrodes and in proportion to the potential difference between the electrodes. Therefore, in this case, too, a high efficiency is obtained by closing the distance between the electrodes. The bending amount of the diaphragm 401 during operation is thus a large factor that determines the ultrasound transmission/reception characteristics. Now, consider a case where the pressure applied to the CMUT has changed. A change in external pressure changes the bending amount of the diaphragm 401 toward the substrate 406 at the state when there is no electrostatic attractive force between the upper and lower electrodes. Consequently, the bending amount of the diaphragm 401 also changes when a predetermined potential difference is applied between the upper and lower electrodes to create a predetermined electrostatic attractive force. The ultrasound transmission/reception characteristics are changed as well to a degree corresponding to the changed bending amount. It is understood from the above that the ultrasound transmission/reception characteristics of the CMUT are easily affected by a change in external pressure.

In this embodiment, the potential applied by the DC potential applying unit 501 is changed based on the transmission/reception correcting signal 307, which is created based on the detected pressure signal 306 from the pressure detecting unit 203, to thereby change the potential difference between the upper and lower electrodes of the CMUT. A change in potential difference between the upper and lower electrodes changes the electrostatic attractive force generated between the electrodes, and changes the bending amount of the diaphragm 401. In this embodiment, the change in bending amount is used to correct or adjust the transmission/reception characteristics of the CMUT. With this structure, the transmission/reception characteristics are corrected precisely despite a change in external pressure, by changing the electrostatic attractive force in small increments. A transducer in which a change in external pressure has less chance of changing the transmission/reception characteristics of the transmitting/receiving unit 201 is thus provided.

As has been described, according to this embodiment, a fluctuation in the transmission/reception characteristics of the transmitting/receiving unit due to pressure applied to the electromechanical transducer is corrected precisely even though a CMUT, which is easily affected by pressure, is used in the transmitting/receiving unit. Therefore, accurate elastic wave information is obtained and a desired elastic wave can be transmitted even when external pressure works on the electromechanical transducer. Another advantage of this embodiment, where a fluctuation in the transmission/reception characteristics of the transmitting/receiving unit is corrected, is that, unlike the first embodiment, there is no need to perform a correction of a transmitted signal which is transmitted to the transmitting/receiving unit and/or a correction of a received signal which is received by the transmitting/receiving unit based on pressure information which is detected by the pressure detecting unit.

Third Embodiment

Figure 2B:
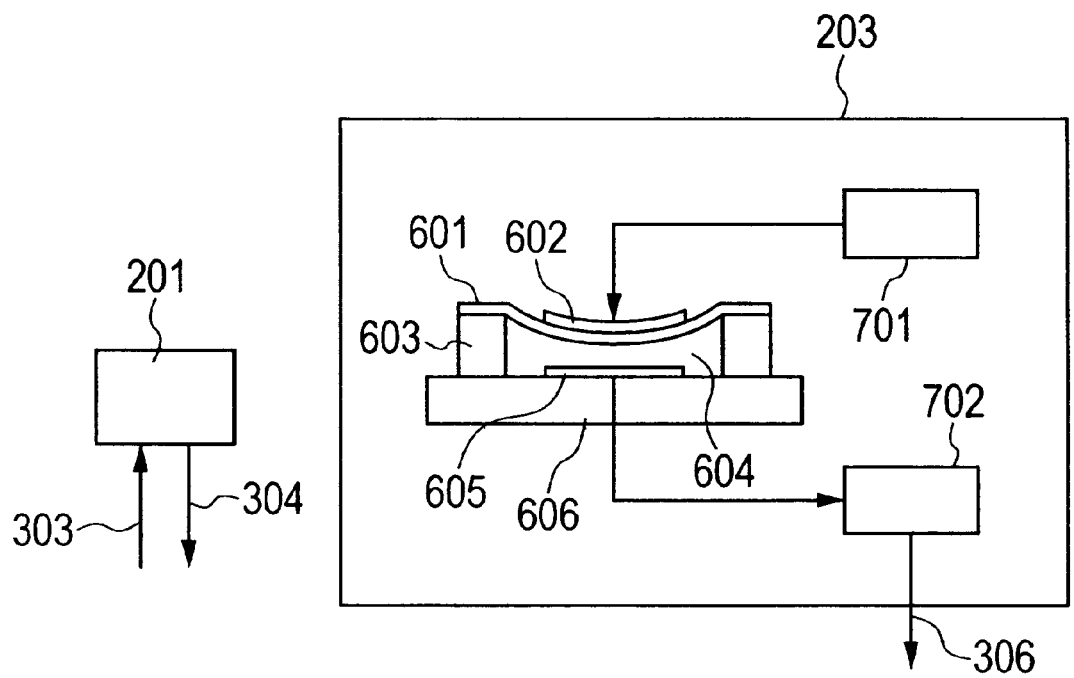
FIG. 2B is a diagram illustrating an electromechanical transducer according to a third embodiment.

A third embodiment is described with reference to FIG. 2B. The difference between the third embodiment and the embodiments described above is the pressure detecting unit 203. The rest of the third embodiment is the same as the first embodiment or the second embodiment. In this embodiment, the pressure detecting unit 203 has frequency characteristics different from the frequency characteristics of the elastic wave transmitting/receiving unit 201.

A CMUT is used in the pressure detecting unit 203 in this embodiment. The pressure detecting unit 203 of this embodiment which is illustrated in FIG. 2B includes a diaphragm 601, an upper electrode 602, supporting portions 603, a gap 604, a lower electrode 605, a substrate 606, a DC potential applying unit 701, and a current detecting unit 702. In the CMUT of the pressure detecting unit 203, the upper electrode 602 is formed on the diaphragm 601, which is supported by the supporting portions 603 formed on the substrate 606. The lower electrode 605 is placed on the substrate 606 so as to face the upper electrode 602, which is formed on the diaphragm 601, via the gap 604.

The mode of the diaphragm 601 is set to a numerical value that facilitates vibration only at a frequency where pressure changes (usually 1 kHz or lower). The mode of the diaphragm 601 is also set so that the diaphragm 601 hardly vibrates in a frequency range where the elastic wave transmitting/receiving unit 201 transmits/receives. The degree of causing the diaphragm 601 to vibrate at a specific frequency input can be set arbitrarily by adjusting the mechanical characteristics of the diaphragm 601 of the CMUT to have an appropriate value. Specifically, the mechanical characteristics of the diaphragm 601 can easily be set by adjusting the physical properties of the diaphragm 601, the structure, thickness, and the size of the diaphragm 601, the distance between the upper and lower electrodes, or other parameters. Also in this case, a DC potential applying unit 701 applies a predetermined DC potential to the upper electrode 602 to create a desired potential difference between the upper electrode 602 and the lower electrode 605. The pressure 305 changes the bending amount of the diaphragm 601, thereby changing the distance (i.e., capacitance) between the electrodes and generating a minute current in the lower electrode 605 through electrostatic induction. The value of the minute current corresponds to the change in the distance between the electrodes. Accordingly, the change in the distance between the electrodes can be detected by measuring the value of the minute current with the current detecting unit 702. The change in the distance between the electrodes is caused by a change in the bending amount of the diaphragm 601 which in turn is caused by a change in the pressure 305 applied to the diaphragm 601. Based on those relations, the detected pressure signal 306 which indicates the magnitude of the pressure 305 applied to the diaphragm 601 may be taken out.

In the structure of this embodiment, the frequency range of frequency characteristics in which the pressure detecting unit 203 responds is set to a low frequency range in order to detect external pressure, unlike a high frequency range of frequency characteristics in which the elastic wave transmitting/receiving unit 201 responds. This enables the pressure detecting unit 203 to take out accurate pressure information without being affected by ultrasound transmission/reception in the transmitting/receiving unit 201. External pressure can thus be detected at the same time ultrasound transmission/reception is executed, and the electromechanical transducer is corrected in real time. Information of an object is therefore obtained quickly, which equals high-speed imaging or imaging at short update intervals (acquisition of moving images). In addition, the use of a CMUT in the pressure detecting unit 203 provides a high degree of freedom in setting frequency characteristics, and it is easy to set optimum frequency characteristics to the pressure detecting unit 203. According to this embodiment, a fluctuation in the transmission/reception characteristics of the transmitting/receiving unit 201 due to pressure applied to the electromechanical transducer is thus corrected quickly. While a CMUT is used in the pressure detecting unit 203, this embodiment is not limited thereto and any element capable of detecting pressure, such as a piezoelectric element, a piezoresistor element, or an element that uses a change in vibration information of a vibrator, can be used as the pressure detecting unit.

Fourth Embodiment

A fourth embodiment is described next with reference to FIG. 3A. The difference between the fourth embodiment and the other embodiments is the pressure detecting unit 203. The rest of the fourth embodiment is the same as any of the first to third embodiments. In this embodiment, a CMUT is used in the pressure detecting unit 203, and the pressure detecting unit 203 detects external pressure with the use of an AC signal having a specific frequency.

Figure 3A:
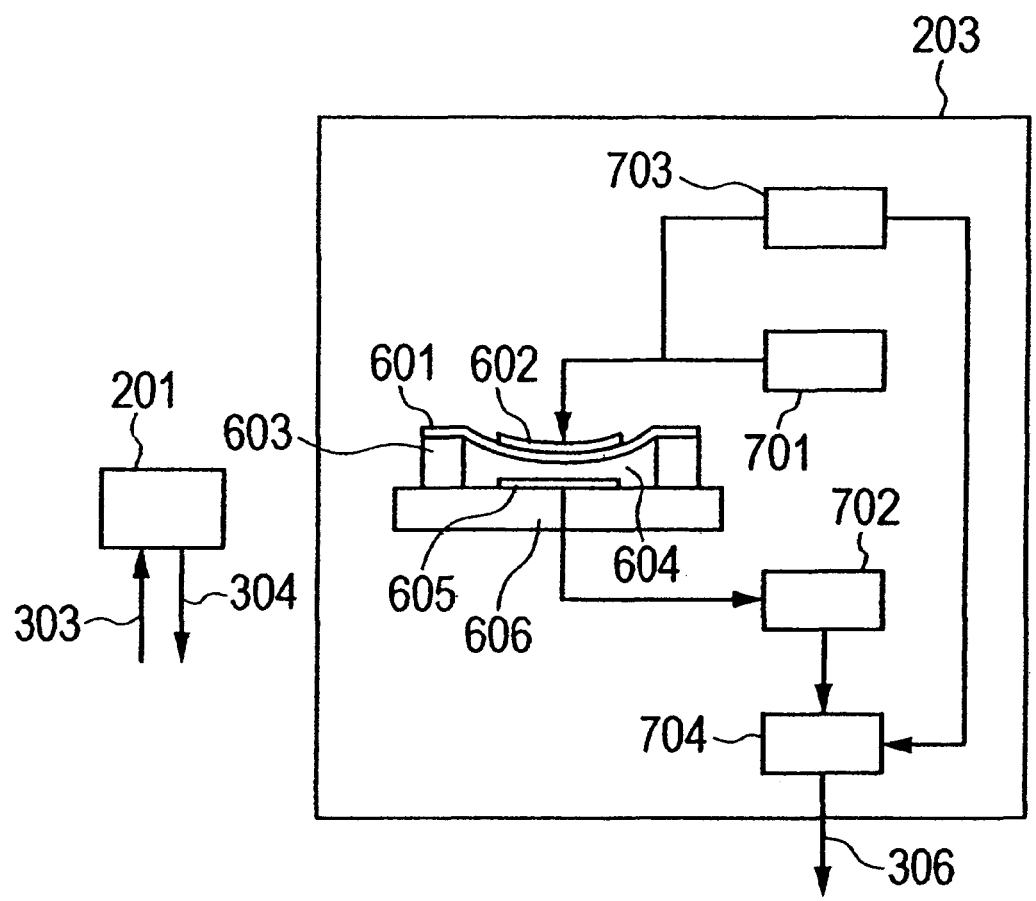
FIG. 3A is a diagram illustrating an electromechanical transducer according to a fourth embodiment.

In FIG. 3A which illustrates an electromechanical transducer of this embodiment, denoted by 703 and 704 are an AC potential multiplexing unit and a pressure signal demodulating unit, respectively. The DC potential applying unit 701 and the AC potential multiplexing unit 703 are connected to the upper electrode 602 of the pressure detecting unit 203. The AC potential multiplexing unit 703 is capable of multiplexing a sine wave potential that has a certain frequency with a potential that is applied to the upper electrode 602. In a potential difference applied between the upper electrode 602 and lower electrode 605 of the pressure detecting unit 203, a sine wave AC potential having a certain frequency is therefore multiplexed with a DC potential. The AC potential multiplexing unit 703 also outputs information of the multiplexed frequency to the pressure signal demodulating unit 704.

A current having a certain signal amplitude that corresponds to the distance between the upper electrode 602 and the lower electrode 605 and modulated with a frequency that is multiplexed by the AC potential multiplexing unit 703 is generated in the lower electrode 605 of the pressure detecting unit 203. This means that the current increases as the distance between the upper and lower electrodes becomes shorter whereas the current decreases as the distance between the upper and lower electrodes grows. The current detecting unit 702 is connected to the lower electrode 605, and detects an input alternating-current, which serves as an AC output signal. The AC output signal output from the current detecting unit 702 is demodulated by the pressure signal demodulating unit 704 with the multiplexed frequency component, and then output as the detected pressure signal 306. In short, the detected pressure signal 306 is detected by a conventional wave detection method.

The frequency of a component multiplexed by the AC potential multiplexing unit 703 is higher than a frequency at which external pressure changes and is outside of a frequency band in which the elastic wave transmitting/receiving unit 201 transmits/receives. To give a more detailed description, firstly, a frequency generated by the AC potential multiplexing unit 703 is higher than a frequency at which external pressure changes. In this embodiment, a multiplexed AC signal is used in a potential between the electrodes in order to measure with higher precision a change in the distance between the upper and lower electrodes (i.e., a change in capacitance) which is caused by a change in external pressure. A change in external pressure occurs at a low frequency (usually 1 kHz or lower), and hence a current detecting method that uses a change in the distance between the electrodes does not always succeed in achieving a satisfactory level of measurement precision. By using an AC signal that is higher than a frequency at which external pressure changes as described above, the current generated in the lower electrode 605 is increased in proportion to this AC frequency. The AC signal is demodulated by the pressure signal demodulating unit 704, and the distance between the electrodes which is correlated to true external pressure information to be obtained can thus be measured with higher precision. The pressure 305 applied to the elastic wave transmitting/receiving unit 201 is accordingly detected with higher precision and the transmission/reception characteristics of the transmitting/receiving unit 201 can be corrected or compensated more finely. In addition, by using an AC frequency higher than a frequency at which external pressure changes, the multiplexed AC potential hardly affects the diaphragm 601 of the pressure detecting unit 203, and the pressure is therefore measured accurately. Secondly, the frequency generated by the AC potential multiplexing unit 703 is outside of a frequency band in which the elastic wave transmitting/receiving unit 201 transmits/receives. The multiplexed AC potential is thus prevented from being affected by transmission/reception performed by the transmitting/receiving unit 201. As a result, external pressure may be detected with precision during the transmission/reception of ultrasound, and the electromechanical transducer may be corrected or compensated accurately in real time.

As described, according to this embodiment, a fluctuation in the transmission/reception characteristics of the elastic wave transmitting/receiving unit 201 due to external pressure applied to the electromechanical transducer may be detected with precision and accurately, and a more precise correction or compensation may be made at high speed.

Fifth Embodiment

A fifth embodiment is described next with reference to FIG. 3B. The difference between the fifth embodiment and the other embodiments is the mechanism of the pressure detecting unit 203. The rest of the fifth embodiment is the same as any of the first to fourth embodiments. An electromechanical transducer of this embodiment includes multiple pressure detecting units 203, pressure at each of the elastic wave transmitting/receiving units 201 arranged into arrays is estimated to correct or compensate the transmission/reception characteristics of each of the transmitting/receiving units 201.

Figure 3B:
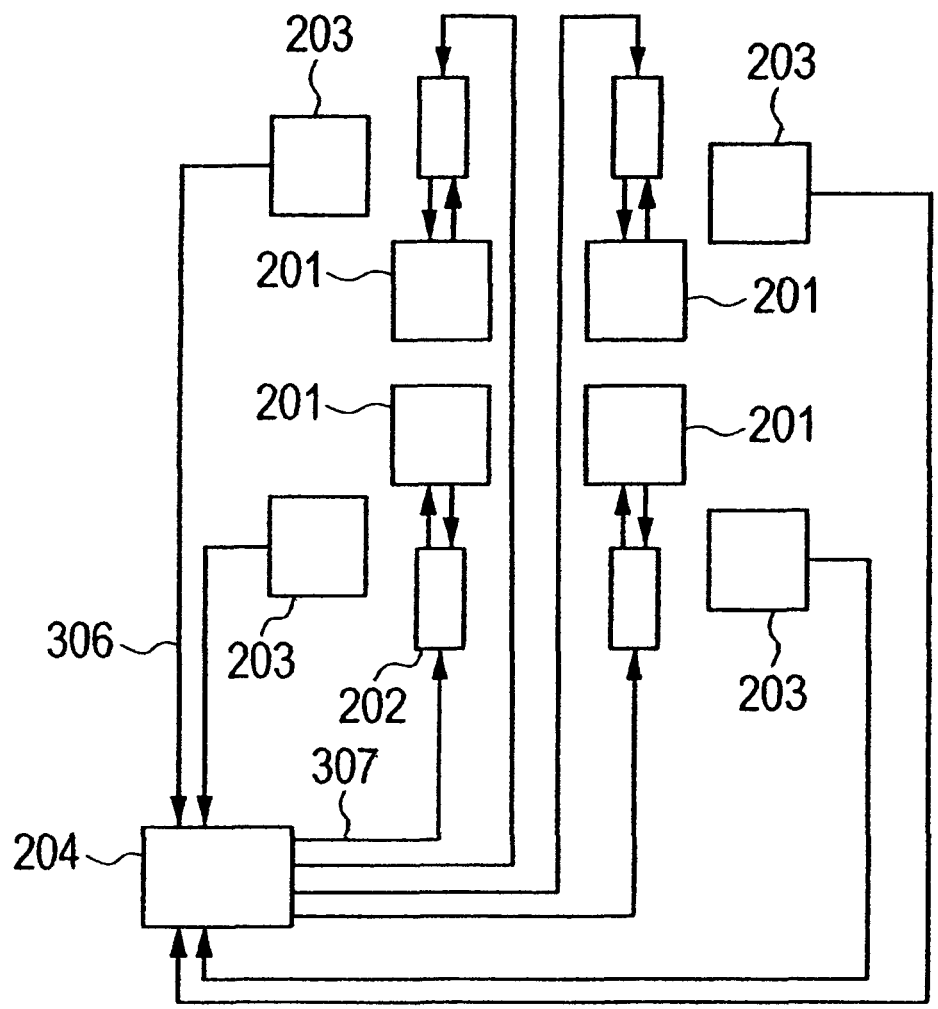
FIG. 3B is a diagram illustrating an electromechanical transducer according to a fifth embodiment.

FIG. 3B illustrating the structure of the electromechanical transducer of this embodiment is a plan view conceptually showing a face of the electromechanical transducer 102 that is in contact with the object 101. The elastic wave transmitting/receiving units 201 here are arranged into two-dimensional arrays (2×2 two-dimensional arrays in FIG. 3B). Multiple pressure detecting units 203 (four in FIG. 3B) are placed around the two-dimensional arrays of the transmitting/receiving units 201. Multiple detected pressure signals 306 detected by the multiple pressure detecting units 203 are input to the transmission/reception characteristics correcting unit 204. From the multiple detected pressure signals 306 and arrangement information of the multiple transmitting/receiving units 201 and the multiple pressure detecting units 203, the correcting unit 204 estimates pressure applied to each of the transmitting/receiving units 201. A change in the ultrasound transmission/reception characteristics of each transmitting/receiving unit 201 in the two-dimensional arrays is thus estimated from information of the multiple pressure detecting units 203.

Based on the estimated information about the transmission/reception characteristics of the respective transmitting/receiving units 201, the transmission/reception correcting signals 307 are output to the respective driving and detected signal processing units 202. Each signal processing unit 202 uses the received output signal to make the ultrasound transmitted signal 303 or the ultrasound received signal 304 reflect the pressure fluctuation information. This process is as described in the first embodiment. The correction method here is the compensation described above which involves correcting a transmitted/received signal. Instead, the correction method described in the second embodiment may be employed in which the transmission/reception characteristics of the transmitting/receiving unit 201 are directly corrected.

According to this embodiment, a fluctuation in transmission/reception characteristics due to external pressure applied to each transmitting/receiving unit 201 is corrected or compensated and, in addition, variations among the arrays of transmitting/receiving units 201 in terms of fluctuation in transmission/reception characteristics due to external pressure are corrected as well.

Sixth Embodiment

A sixth embodiment is described next with reference to FIG. 4. The sixth embodiment is an ultrasound measuring device that uses the electromechanical transducer according to one of the first to fifth embodiments. In this embodiment, signal correction based on the detected pressure information 306 is executed in imaging as well in addition to correcting or compensating the transmission/reception characteristics of the elastic wave transmitting/receiving unit 201.

Figure 4:
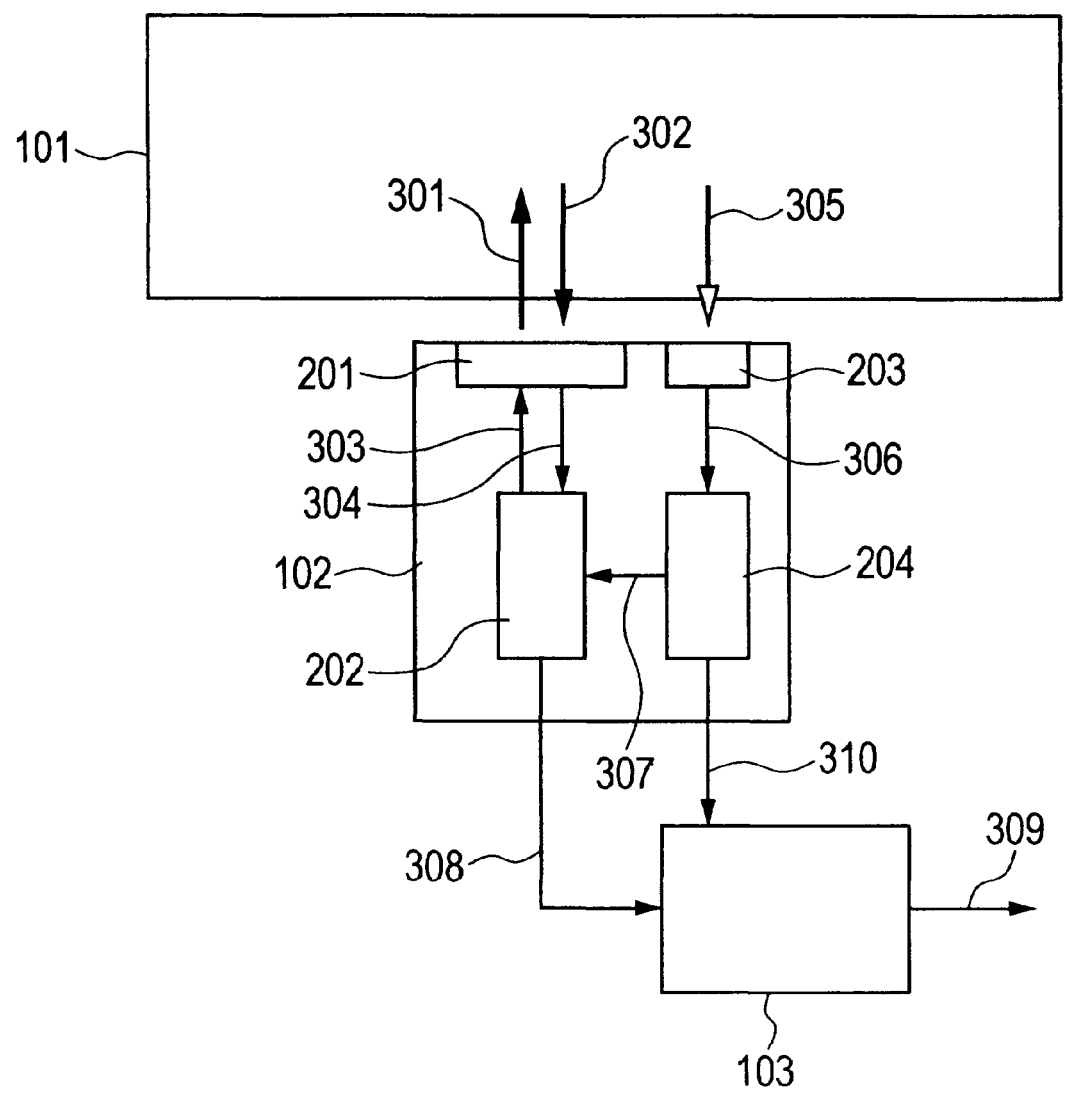
FIG. 4 is a diagram illustrating an ultrasound measuring device according to a six embodiment which includes an electromechanical transducer.

FIG. 4 illustrates the ultrasound measuring device of this embodiment which uses the electromechanical transducer of the present invention. As illustrated in FIG. 4, the transmission/reception characteristics correcting unit 204 in this embodiment outputs the image correcting signal 310 to the imaging unit 103 and, when imaging is executed, the imaging information signal 308 is corrected. With this structure, the imaging information signal 308 which is original information to be imaged is corrected separately by the driving and detected signal processing unit 202 and, in addition, the whole image to be imaged is corrected. In other words, when there is a component that is not corrected satisfactorily at the stage of correcting or compensating the transmission/reception characteristics of the elastic wave transmitting/receiving unit 201, or at the stage of processing a received signal, the component that has not been corrected satisfactorily is corrected by performing signal correcting processing at the stage of forming the whole image. An image of even higher precision is thus obtained.

According to this embodiment, a complex correction can be made and the measuring device provided is capable of correcting a fluctuation in transmission/reception characteristics due to external pressure and variations in terms of transmission/reception characteristics fluctuation on an even higher level. Note that, while the electromechanical transducer 102 of the first embodiment is used in the example of FIG. 4, the measuring device can also use the electromechanical transducers of the other embodiments.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-282279, filed Dec. 11, 2009, which is hereby incorporated by reference herein in its entirety.

The invention claimed is:

1. An electromechanical transducer comprising:
   an elastic wave transmitting/receiving unit which transmits/receives an elastic wave;
   a pressure detecting unit which detects pressure applied the pressure detecting unit; and
   a correcting unit which, based on pressure information detected by the pressure detecting unit, performs at least one of a correction of elastic wave transmitted/received signals relevant to the elastic wave transmitting/receiving unit and a correction of transmission/reception characteristics of the elastic wave transmitting/receiving unit
   wherein the pressure detecting unit is different from the elastic wave transmitting/receiving unit, and the pressure detecting unit has frequency characteristics that respond to pressure of a frequency that is lower than a frequency range in frequency characteristics of the elastic wave transmitting/receiving unit.

2. An electromechanical transducer according to claim 1, wherein the elastic wave transmitting/receiving unit comprises a capacitive transducer that comprises multiple electrodes facing each other via a gap, and
   wherein the correcting unit corrects the transmission/reception characteristics of the elastic wave transmitting/receiving unit by changing electrostatic attractive force between the multiple electrodes.

3. An electromechanical transducer according to claim 1, wherein the correcting unit corrects at least one of an elastic wave transmitted signal which is transmitted to the elastic wave transmitting/receiving unit, and an elastic wave received signal which is received by the elastic wave transmitting/receiving unit.

4. An electromechanical transducer according to claim 1, wherein the pressure detecting unit comprises a capacitive transducer that comprises multiple electrodes facing each other across a gap.

5. An electromechanical transducer according to claim 1, wherein the pressure detecting unit comprises:
   a capacitive transducer that comprises multiple electrodes facing each other across a gap;
   a modulating unit which modulates a capacitance between the multiple electrodes of the capacitive transducer with a signal having a predetermined frequency; and a demodulating unit which uses the signal having the predetermined frequency to demodulate a current signal from the capacitive transducer where the signal having the predetermined frequency is multiplexed, wherein the predetermined frequency is higher than a frequency range in the frequency characteristics of the pressure detecting unit, and is outside the frequency range in the frequency characteristics of the elastic wave transmitting/receiving unit.

6. An electromechanical transducer according to claim 1, wherein the electromechanical transducer comprises multiple elastic wave transmitting/receiving units and multiple pressure detecting units, and wherein the correcting unit performs the correction for each of the multiple elastic wave transmitting/receiving units based on pieces of pressure information detected respectively by the multiple pressure detecting units.

7. A measuring device, comprising:
the electromechanical transducer of claim 1, and
an imaging unit for imaging an object by correcting an imaging information signal, which is created based on an elastic wave received signal from the electromechanical transducer, with an image correcting signal, which is created based on pressure information from the electromechanical transducer.

8. An electromechanical transducer according to claim 1, wherein the surface of the pressure detecting unit detecting the pressure applied to the pressure detecting unit and the surface of the elastic wave transmitting/receiving unit transmitting/receiving an elastic wave locate in different positions in the same plane.

9. An electromechanical transducer according to claim 1, wherein the correcting unit corrects at least one of transmission characteristics of the elastic wave transmitting/receiving unit and reception characteristics of the elastic wave transmitting/receiving unit.

10. An electromechanical transducer comprising:
an elastic wave transmitting/receiving unit which transmits and/or receives an elastic wave;
a pressure detecting unit which detects pressure applied to the pressure detecting unit; and
a correcting unit which, based on pressure information detected by the pressure detecting unit, performs at least one of a correction of elastic wave transmitted/received signals relevant to the elastic wave transmitting/receiving unit and a correction of transmission/reception characteristics of the elastic wave transmitting/receiving unit,
wherein the pressure detecting unit is different from the elastic wave transmitting/receiving unit.

11. An electromechanical transducer according to claim 10, wherein the elastic wave transmitting/receiving unit comprises a capacitive transducer that comprises multiple electrodes facing each other via a gap, and
wherein the correcting unit corrects the transmission/reception characteristics of the elastic wave transmitting/receiving unit by changing electrostatic attractive force between the multiple electrodes.

12. An electromechanical transducer according to claim 10, wherein the correcting unit corrects at least one of an elastic wave transmitted signal which is transmitted to the elastic wave transmitting/receiving unit, and an elastic wave received signal which is received by the elastic wave transmitting/receiving unit.

13. An electromechanical transducer according to claim 10, wherein the pressure detecting unit comprises a capacitive transducer that comprises multiple electrodes facing each other across a gap.

14. An electromechanical transducer according to claim 10,
wherein the pressure detecting unit comprises:
a capacitive transducer that comprises multiple electrodes facing each other across a gap;
a modulating unit which modulates a capacitance between the multiple electrodes of the capacitive transducer with a signal having a predetermined frequency; and
a demodulating unit which uses the signal having the predetermined frequency to demodulate a current signal from the capacitive transducer where the signal having the predetermined frequency is multiplexed,
wherein the predetermined frequency is higher than a frequency range in the frequency characteristics of the pressure detecting unit, and is outside the frequency range in the frequency characteristics of the elastic wave transmitting/receiving unit.

15. An electromechanical transducer according to claim 10,
wherein the electromechanical transducer comprises multiple elastic wave transmitting/receiving units and multiple pressure detecting units, and
wherein the correcting unit performs the correction for each of the multiple elastic wave transmitting/receiving units based on pieces of pressure information detected respectively by the multiple pressure detecting units.

16. An electromechanical transducer according to claim 10, wherein the surface of the pressure detecting unit detecting the pressure applied to the pressure detecting unit and the surface of the elastic wave transmitting/receiving unit transmitting/receiving an elastic wave locate in different positions in the same plane.

17. An electromechanical transducer according to claim 10, wherein the correcting unit corrects at least one of transmission characteristics of the elastic wave transmitting/receiving unit and reception characteristics of the elastic wave transmitting/receiving unit.

18. A measuring device, comprising:
the electromechanical transducer of claim 10, and
an imaging unit for imaging an object by correcting an imaging information signal, which is created based on an elastic wave received signal from the electromechanical transducer, with an image correcting signal, which is created based on pressure information from the electromechanical transducer.

* * * * *